(12) United States Patent
Lee et al.

(10) Patent No.: US 6,222,051 B1
(45) Date of Patent: Apr. 24, 2001

(54) ALPHA-TOCOPHEROL 4-AMINOBENZOIC ACID ESTER COMPOUNDS AND METHOD FOR PREPARING THE SAME

(75) Inventors: Si-Joon Lee; Hee-Young Jung, both of Taejon (KR)

(73) Assignee: SK Corporation, Seoul (KR)

( * ) Notice: Subject to any disclaimer, the term of this patent is extended or adjusted under 35 U.S.C. 154(b) by 0 days.

(21) Appl. No.: 09/403,352

(22) PCT Filed: Apr. 28, 1998

(86) PCT No.: PCT/KR98/00103

§ 371 Date: Oct. 18, 1999

§ 102(e) Date: Oct. 18, 1999

(87) PCT Pub. No.: WO98/49154

PCT Pub. Date: Nov. 5, 1998

(30) Foreign Application Priority Data

Apr. 28, 1997 (KR) .................................................. 97-15961

(51) Int. Cl.$^7$ .................................................. C07D 311/72
(52) U.S. Cl. ............................................. 549/410; 549/412
(58) Field of Search ....................................... 549/410, 412

(56) References Cited

FOREIGN PATENT DOCUMENTS 166 221 A2 * 1/1986 (EP) .

* cited by examiner

*Primary Examiner*—Joseph K. McKane
*Assistant Examiner*—Taofiq A. Solola
(74) *Attorney, Agent, or Firm*—Abelman, Frayne & Schwab

(57) ABSTRACT

Alpha-tocopherol 4-aminobenzoate compounds, represented by formula (I), are prepared by the esterification of alpha-tocopherol with 4-aminobenzoic acid. The esters are converted into the element compounds in vivo, so that they have alpha-tocopherol's biological effect including antioxidation as well as the pharmaceutical and biological effects of 4-aminobenzoic acid, including the promotion of red blood cell formation and metabolism, the role of a growth stimulating factor, keeping the skin healthy, and the prevention of hair decoloration. In said formula (I) $R_1$ and $R_2$ which may be the same or different, each is a hydrogen atom or a linear or branched $C_1 \sim C_4$ alkyl chain.

8 Claims, 2 Drawing Sheets

ALPHA-TOCOPHEROL 4-AMINOBENZOIC ACID ESTER COMPOUNDS AND METHOD FOR PREPARING THE SAME

This application is a 371 of PCT/KR98/00103 filed Apr. 28, 1998.

TECHNICAL FIELD

The present invention relates, in general, to novel alpha-tocopherol 4-aminobenzoic acid ester compounds and to a method for preparing the same and, more particularly, to novel alpha-tocopherol 4-aminobenzoic acid ester compounds which have the biological effects of alpha-tocopherol and 4-aminobenzoic acid, both, in vivo and to a method for preparing the same.

BACKGROUND ART 4-aminobenzoic acid derivatives are generally represented by the following formula II:

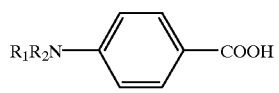

(II)

wherein $R_1$ and $R_2$, which may be the same or different, each is a hydrogen atom or a linear or branched $C_1$~$C_4$ alkyl chain.

Of the compounds represented by the formula II, the 4-aminobenzoic acid in which $R_1$ and $R_2$ each is a hydrogen atom, is now found to play a role as a growth-promoting factor and to have a pharmacological activity of helping in the formation of red blood cells and the metabolism of the human body. In addition, it is reported that the 4-aminobenzoic acid aids to maintain healthy skin and to prevent the decoloration of the hair.

Vitamin E (DL-alpha-tocopherol), represented by the following formula III, is widely used as an antioxidant for living organisms:

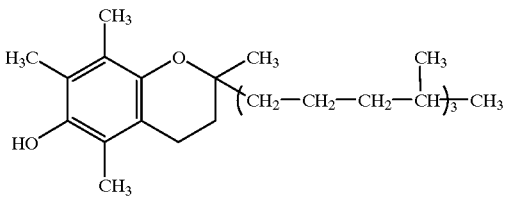

(III)

Recently, vitamin E has been recognized to be clinically effective in various fields and the demand for vitamin E is increasing. As seen in the formula III, free tocopherol, a compound possessing a benzene ring to which hydroxy group binds, is unstable because it itself is easily oxidized in vitro.

Tocopherol quinone, an oxidized product of vitamin E, no longer has the biological activity of vitamin E. Thus, in order to prevent the in vitro oxidation of vitamin E, it must be converted to other derivative forms which conserve the biological activity of vitamin E. Representatives are esters. Examples of such esters include α-tocopherol acetate, α-tocopherol acid succinate, and α-tocopherol palmitate. These derivatives are advantageous in storage and transportation because they are stable relative to free α-tocopherol itself.

Because these esters have pharmaceutically acceptable stability in addition to being very easy to handle, they are effectively used as replacements for α-tocopherol. Upon oral administration, the vitamin E esters are absorbed into the intestinal track and hydrolyzed completely, that is, into free tocopherol and acids by pancreatic enzymes and intestinal enzymes. Thus, the vitamin E esters are absorbed in the form of free tocopherol into the living body. In other words, the vitamin E esters are converted into free vitamin E by digestive enzymes in the living body, so that the biological effect they have on the living body is practically equivalent to that of vitamin E.

DISCLOSURE OF THE INVENTION

Therefore, it is an object of the present invention to provide novel pharmaceutically active compounds which have the equal biological activity to that of vitamin E but a more beneficial effect on the living body.

It is another object of the present invention to provide a method for preparing such a type of compounds.

In accordance with an embodiment of the present invention, there is provided a type of compounds represented by the following formula I:

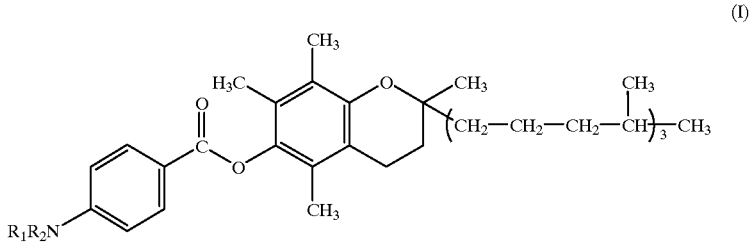

(I)

wherein $R^1$ and $R^2$, which may be the same or different, each is a hydrogen atom or a linear or branched $C_1$~$C_4$ alkyl chain.

In accordance with another embodiment of the present invention, there is provided a method for preparing the compound of the formula I, in which a 4-aminobenzoic acid derivative, represented by the following formula II:

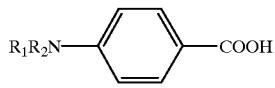

(II)

wherein $R_1$ and $R_2$ are as defined above, is reacted with an alpha-tocopherol, represented by the following formula III:

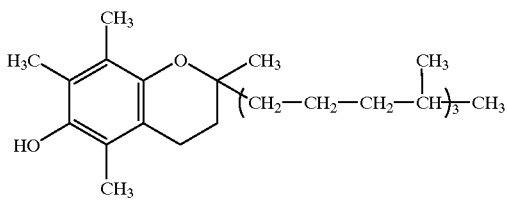

(III)

in a reaction solvent and in the presence of a base catalyst.

BEST MODE FOR CARRYING OUT THE INVENTION

Figure 1:
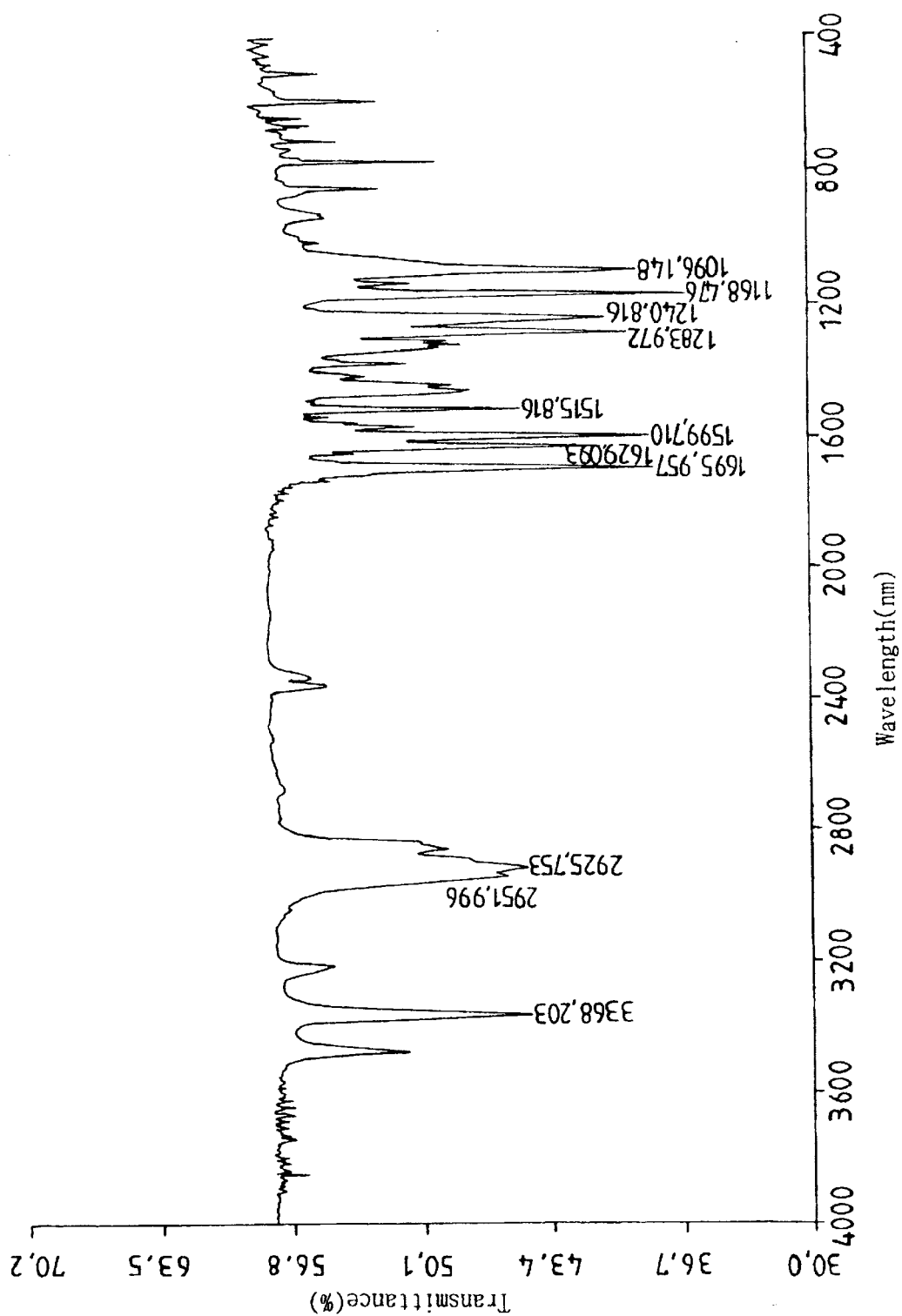
FIG. 1 shows an infrared adsorption spectrum spectroscopy of the compound prepared according to Example I.

The compounds of the formula I, consisting of 4-aminobenzoic acid and alpha-tocopherol, are a kind of representative esters but, to our knowledge, the novel compounds which have not been reported, thus far.

These novel compounds may be prepared by the esterification of alpha-tocopherol with 4-aminobenzoic acid halide. A useful 4-aminobenzoic acid halide may result from the reaction of thionyl chloride with 4-aminobenzoic acid, N-linear or branched alkyl containing at least one carbon atom-4-aminobenzoic acid or N,N'-di(linear or branched alkyl containing at least one carbon atom) and preferably with 4-benzoic acid, N-methyl substituted 4-aminobenzoic acid or N,N'-dimethyl substituted 4-aminobenzoic acid, as shown in the following reaction scheme I:

Reaction Scheme I

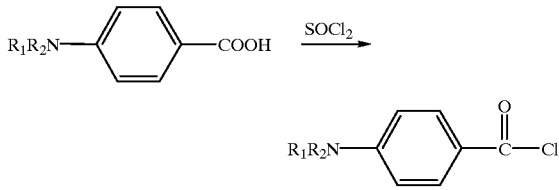

wherein $R_1$ and $R_2$ are as defined above.

The 4-aminobenzoic acid halide was prepared by using a modification of procedure described in a previous literature (ZCM, 1982, 178). Without using a particular solvent, the reaction was carried out: thionyl chloride was used as a reactant as well as a solvent. After completion of the reaction, unreacted thionyl chloride and hydrochloric acid, the by-product, were removed by heating and the residue was distilled in vacuo to obtain 4-aminobenzoic acid halide.

The preparation of the alpha-tocopherol 4-aminobenzoate represented by the formula I is shown in the following reaction scheme II:

Reaction Scheme II

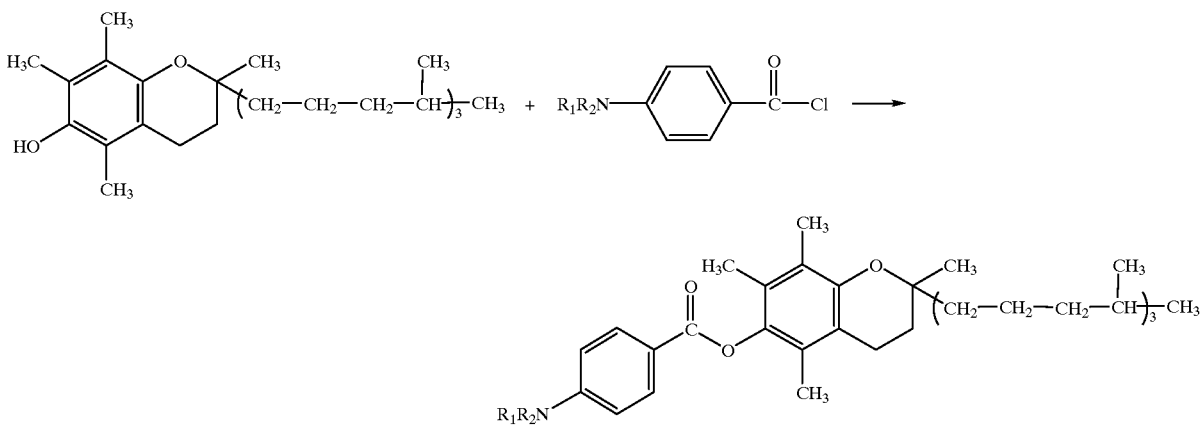

wherein $R_1$ and $R_2$ are as defined above. This reaction can be effectively carried out in the presence of a basic catalyst in an aprotic, halo-organic solvent. Dichloromethane is a preferable solvent. Aprotic, non halo-organic solvents, such as benzene and toluene, do not allow the reaction to proceed at all.

As for the basic catalyst, it can be possible to use pyridine, pyridine/4-(dimethylamino)pyridine or triethylamine. While the first two show similar reaction rate and yield each other, on the other hand triethylamine shows relatively poor in reaction rate and yield.

In the present invention, the molar ratio of the reactants and the basic catalyst; that is of alpha-tocopherol:4-aminobenzoic acid halide:pyridine, is in a range of 1.0:1.1–5.0:2.5–9.0 and preferably 1.0:2.0–3.0:6.0–8.5. This reaction is carried out at a temperature range from 0° C. to the boiling point of the solvent, that is, 40–41° C. and preferably from room temperature to 35° C.

Until 5 hours after the initiation, the reaction proceeded rapidly. But, from then on, the reaction becomes slow in progress and came to the end at 48 hours after the initiation. No more progress in the reaction occurred after 48 hours stirring. Hence, it is preferred for the reaction to be carried out for about 36–48 hours.

The objective product may be isolated and purified through solvent extraction from the reaction mixture, column chromatography and/or recrystallization. Where undissolved products are present in the reaction mixture, they are first removed by filtration, followed by the purification for the final product through the same techniques. The purification is possible by recrystallization alone, without using column chromatography. In this case, the purification is significantly simplified, but purification yield becomes poor.

A better understanding of the present invention may be obtained in light of the following examples which are set forth to illustrate, but are not to be construed to limit the present invention.

EXAMPLE I

Preparation of Alpha-tocopherol 4-aminobenzoate (1)

In a round-bottom flask, 4-aminobenzoic acid (15 g, 0.11 moles) was dissolved in thionyl chloride (23.7 ml, 0.33 moles) and refluxed at 80–90° C. for 4 hours under a nitrogen atmosphere. After completion of the reaction, hydrochloric acid, a by-product, and un-reacted thionyl chloride were removed by vacuum distillation to give a yellow crude product. The purification of the crude product through vacuum distillation gave 4-aminobenzoic acid halide (13 g) as a yellow crystal: Yield 75%. Its structure was confirmed with the aid of proton nuclear magnetic resonance ($^1$H-NMR) spectroscopy and mass spectroscopy. m.p.: 31° C., b.p.: 120° C./12 mbar.

Synthetic alpha-tocopherol (0.7 g, 16 mmol) and the 4-aminobenzoic acid halide obtained above (0.5 g, 32 mmol) were dissolved in dichloromethane (50 ml), followed by adding with pyridine (1.1 ml, 137 mmol) and a basic catalyst, and stirred at room temperature under a nitrogen atmosphere to carry out an esterification reaction. The progress of the esterification was monitored by a thin layer chromatography. It was found that the esterification did not proceed after 48 hours any more since the stirring. Henceforth, the dichloromethane solvent was removed from the reaction mixture by use of a rotary evaporator. The residue was dissolved in ethylacetate and washed several times with a saturated aqueous solution of anhydrous sodium carbonate and then, several times with water. The resulting organic layer was dried over magnesium sulfate and filtered, followed by isolation and purification through column chromatography on silica gel eluting with hexane/ethylacetate mixture (2:1, v/v) to afford alpha-tocopherol 4-aminobenzoate as a pale yellow solid (0.63 g): Yield 70%.

Recrystallization was helpful to obtain more pure products. The recrystallization using ethylacetate and hexane produced pure alpha-tocopherol 4-aminobenzoate (0.49 g, yield 55%) as a pale yellowish white solid.

Without using column chromatography, a pure alpha-tocopherol 4-aminobenzoate could be obtained only by recrystallization using various solvents. First, the crude product was clearly dissolved in iso-propyl alcohol by heating and then, cooled to room temperature to give a solid. The resultant precipitate was filtered and well washed with hexane. One more crystallization using hexane/ethylacetate was performed for the precipitate, followed by vacuum drying to produce pure alpha-tocopherol 4-aminobenzoate: Yield 30%.

Figure 2:
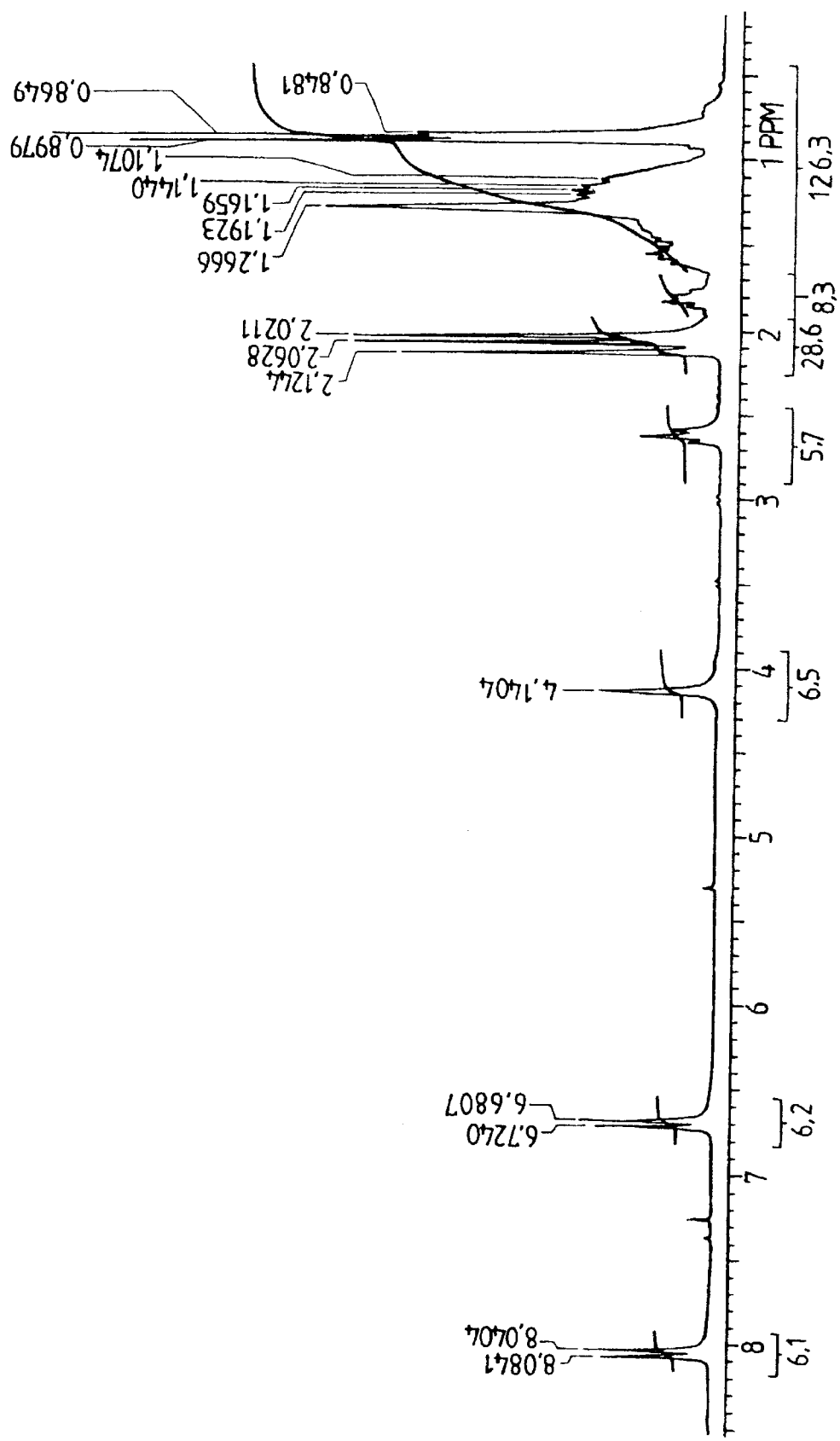
FIG. 2 shows an $^1$H-NMR spectrum of the compound prepared according to Example I.

The structure of the product was identified by infrared chromatography. (FIG. 1), $^1$H-NMR (FIG. 2), and mass spectroscopy.

Element Analysis ($C_{36}H_{55}NO_3$): Calculated: C=78.64%, H=10.08%, N=2.55%. Found: C=79.71%, H=10.09%, N=2.58%.

EXAMPLE II

Preparation of Alpha-tocopherol 4-aminobenzoate (2)

The reaction of alpha-tocopherol with 4-aminobenzoic acid chloride was carried out in the same manner with Example I, except that 10 mol % of 4-(dimethylamino)pyridine was added together with pyridine. This reaction was confirmed to proceed in a similar pattern to that of Example I as measured by thin layer chromatography. The remaining processes of Example I were repeated to produce alpha-tocopherol 4-aminobenzoate (0.61 g, yield 68%).

EXAMPLE III

Preparation of 4-Aminobenzoic Acid Alpha-tocopherol Ester (3)

Alpha-tocopherol 4-aminobenzoate was prepared in the same manner with Example I, except for using triethylamine, instead of pyridine, as a basic catalyst.

Thin layer chromatography monitored the progress of the synthesis, showing that, by one hour after the addition of the reactants, 4-aminobenzoic acid halide was obtained at about 50% of the total amount finally synthesized and, from then on, the reaction rate was rapidly decreased and, after 24 hours had passed since the addition, there occurred no remarkable advance in the reaction. After reaction for 48 hours, the remaining processes of Example I were repeated to produce alpha-tocopherol 4-aminobenzoate with a yield of 59%.

EXAMPLE IV

Preparation of alpha-tocopherol 4-aminobenzoate (4)

The procedure of Example III was repeated, except that 2 equivalents of 4-aminobenzoic acid halide were further added to be the final amount of 4 equivalents.

Thin layer chromatography showed that the conversion rate of the reaction increased a little depending on time but there was no advance after 48 hours. However, by-products were detected with relatively small amounts. After reaction for 48 hours, alpha-tocopherol 4-aminobenzoate was produced with a yield of 65% by following the remaining processes of the Example I.

EXAMPLE V

Preparation of Alpha-tocopherol 4-N-methylaminobenzoate

4-N-methylaminobenzoate halide was synthesized in a similar manner to that of Example I, using 4-N-methylaminobenzoic acid instead of 4-aminobenzoic acid. The procedure for the esterification of alpha-tocopherol with the 4-N-methylaminobenzoic acid halide, and the purification and isolation of the crude product were performed as in Example I, to produce the titled compound (65% yield).

EXAMPLE VI

Preparation of Alpha-tocopherol 4-N,N'-dimethylaminobenzoate

4-N,N'-dimethylaminobenzoic acid halide was synthesized in a similar manner to that of Example I, using 4-N,N'-dimethylaminobenzoic acid instead of 4-aminobenzoic acid. The procedure for the esterification of alpha-tocopherol with the 4-N,N'-dimethylaminoenzoic acid halide, and the purification and isolation of the crude product were performed as in Example I, to produce the titled compound (Yield 58%).

Industrial Applicability

As described hereinbefore, the compounds according to the present invention are a kind of fat-soluble vitamin E precursors, which are adducts of alpha-tocopherol and 4-aminobenzoic acid. Being resistant to external factors, especially, oxidation, they are digested into the components in vivo, so that they can have alpha-tocopherol's biological effect including antioxidation as well as the pharmaceutical and biological effects of 4-aminobenzoic acid, including the promotion of red blood cell formation and metabolism, the role of a growth stimulating factor, keeping the skin healthy, and the prevention of hair decoloration. Consequently, the compounds of the invention are novel vitamin E esters which have never been reported, showing various functions in vivo.

The present invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A method for preparing an alpha-tocopherol 4-aminobenzoate compound represented by the following formula I, comprising reacting 4-aminobenzoic acid derivative represented by the following formula II with an alpha-tocopherol represented by the following formula III in dichloromethane in the presence of a basic catalyst:

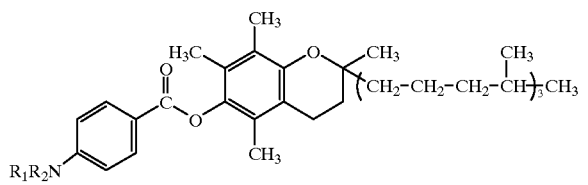
(I)

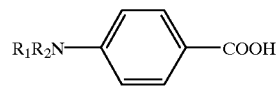
(II)

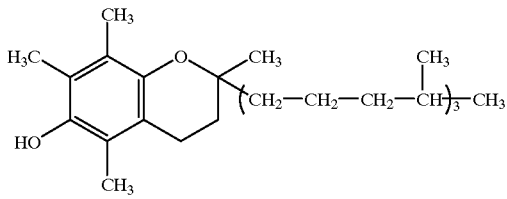
(III)

wherein $R^1$ and $R^2$, which may be the same or different, each is a hydrogen atom or a linear or branched $C_1$–$C_4$ alkyl chain.

2. The method in accordance with claim 1, wherein said basic catalyst is selected from the group consisting of pyridine, pyridine/4-(dimethylamino)pyridine and triethylamine.

3. The method in accordance with claim 1, wherein the alpha-tocopherol, the 4-aminobenzoic acid derivative and the basic catalyst are present at a molar ratio of 1.0:1.1–5.0:2.5–9.0.

4. The method in accordance with claim 3, wherein the alpha-tocopherol, the 4-aminobenzoic acid derivative and the basic catalyst are present at a molar ratio of 1.0:2.0–3.0:6.5–8.5.

5. The method in accordance with claim 1, wherein the reaction is carried out at a temperature 0–41° C. for 36–48 hours.

6. The method in accordance with claim 1, wherein $R_1$ and $R_2$, each is a hydrogen atom.

7. The method in accordance with claim 1, wherein $R_1$ is a hydrogen atom and $R_2$ is a linear or branched $C_1$–$C_4$ alkyl chain.

8. The method in accordance with claim 1, wherein $R_1$ and $R_2$ each is a linear or branched $C_1$–$C_4$ alkyl chain.

* * * * *